United States Patent [19]

Schneider

[11] Patent Number: 4,760,206
[45] Date of Patent: Jul. 26, 1988

[54] PROCESS FOR REMOVING BUTADIENE FROM VINYL CHLORIDE IN A QUENCH TOWER

[75] Inventor: Wolfgang W. Schneider, Broadview Heights, Ohio

[73] Assignee: The B. F. Goodrich Company, Akron, Ohio

[21] Appl. No.: 920,007

[22] Filed: Oct., 1986

[51] Int. Cl.[4] .................... C07C 17/34; C07C 17/38; C07C 21/06

[52] U.S. Cl. .................................. 570/220; 570/226; 570/238

[58] Field of Search ................ 570/226, 220, 238, 262

[56] References Cited

U.S. PATENT DOCUMENTS

| | | | |
|---|---|---|---|
| 3,801,660 | 4/1974 | Coppens | 570/238 |
| 3,876,714 | 4/1975 | Coppens | 570/238 |
| 3,903,182 | 9/1975 | Rechmeier et al. | 570/226 |
| 3,920,761 | 11/1975 | Krome | 570/226 |
| 4,049,729 | 9/1977 | Otto et al. | 570/238 |
| 4,060,460 | 11/1977 | Smalley et al. | 570/262 |

Primary Examiner—J. E. Evans

[57] ABSTRACT

Ferric chloride ($FeCl_3$), a known chlorination and polymerization catalyst for 1,3-butadiene ("BD"), can nevertheless be effectively used in a packed or trayed quench tower, operating under essentially anhydrous conditions, without plugging it. Essentially all BD from a crude stream of vinyl chloride (VCl), is removed within a hold-up time of 6 minutes. The speed of removal is note-worthy because less than half the stoichiometric amount of chlorine required to chlorinate the BD is used. The BD is preferentially chlorinated, the time being too short to chlorinate a substantial amount of chloroprene and monovinylacetylene. Only a portion of the BD is removed by chlorination, the remainder being removed by polymerization catalyzed by 100–200 ppm anhydrous $FeCl_3$. For such speed and effectiveness without plugging the quench tower, the amount of BD in the effluent stream is required to be controlled to no more than 100 ppm, based on the weight of 1,2-dichloroethane (ethylene dichloride or "EDC") in the stream.

3 Claims, 1 Drawing Sheet

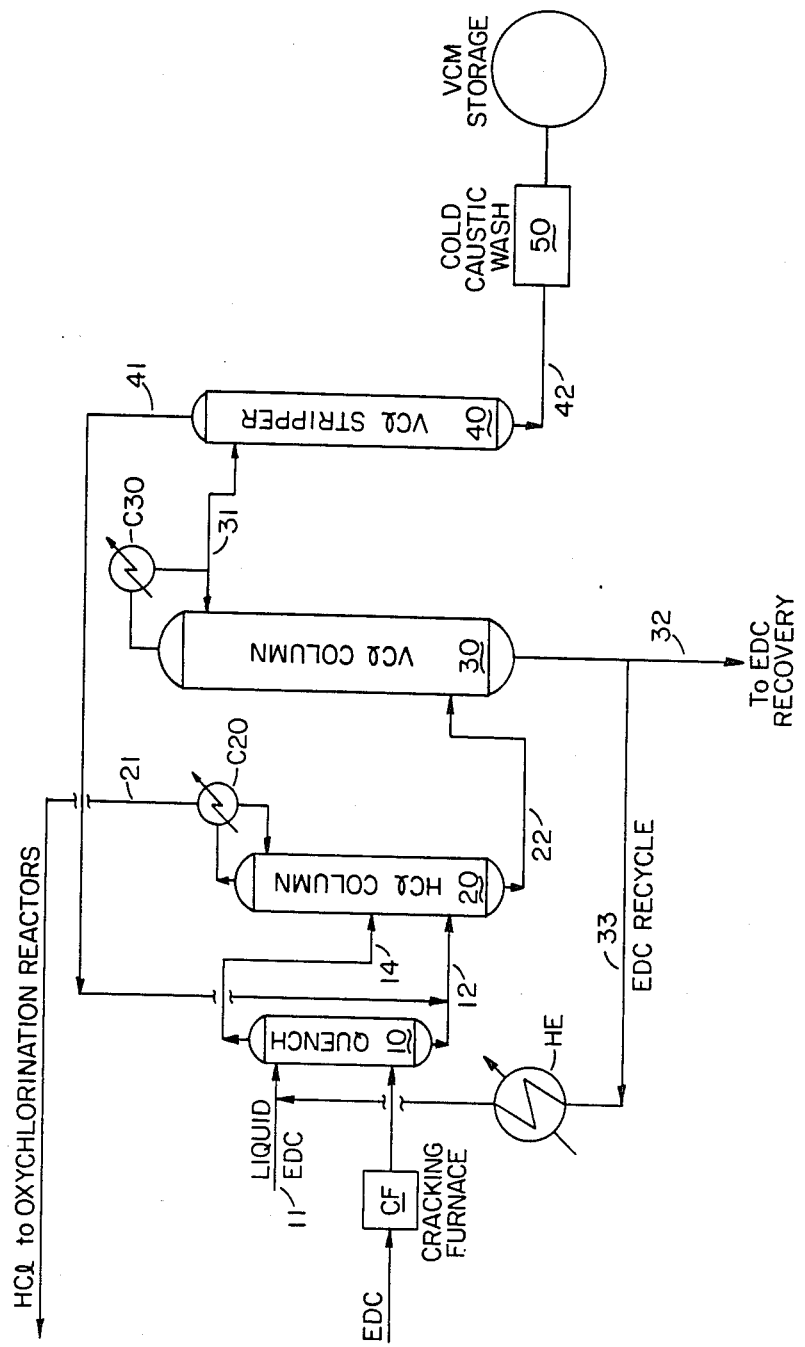

PROCESS FOR REMOVING BUTADIENE FROM VINYL CHLORIDE IN A QUENCH TOWER

BACKGROUND OF THE INVENTION

Few monomers are commercially produced in the world on so large a scale as vinyl chloride monomer ("VCM"). The U.S. production alone of VCM was about 7.7 billion pounds in the year 1984, most of which was used in the production of poly(vinyl chloride), the remainder was used for the production of copolymers of VCM with vinylidene chloride, graft copolymers of vinyl chloride on methylmethacrylate, polybutadiene, ethylene-propylene elastomer, etc.

Despite this scale of production, not much attention has been accorded the exacting requirements for the commodity VCM, except of course by those charged with the responsibility of producing on-spec product VCM. Product VCM, referred to as "finished" VCM, is limited to the following: HCl 0.5 parts per million (ppm) by weight; acetylene ($C_2H_2$) 0.2 ppm; caustic (NaOH) 0.3 ppm; butadiene 10 ppm; and, water 100 ppm. The presence of water is undesirable because it causes corrosion in steel shipping containers and storage vessels, generating ferric chloride which seriously interferes with polymerization reactions with the VCM.

As of the present time, VCM produced in a conventional commercial VCM plant is derived from vinyl chloride ("VCl") in the overhead of a VCl distillation column which overhead typically contains from about 50-500 ppm HCl and 10-300 ppm water. This VCl overhead, after it is condensed, is stripped in a stripping column to reduce the level of HCl which is taken overhead. The bottoms from the stripper, still containing in the range from about 1-50 ppm HCl, is scrubbed either by contact with caustic solution, or by upflow percolation through a bed of solid caustic.

For the purpose of clarity, the term "vinyl chloride" (VCl) is used herein when the vinyl chloride is in-process, that is, first formed and subsequently processed in the VCl purification section. The term "vinyl chloride monomer" (VCM) is used when the VCl has been purified, that is finished, so that it meets product VCM specifications.

Those operating a VCM plant utilizing such a process, recognize that corrosion is the overriding problem in the stripping column. This problem is exacerbated because the corrosion process contributes ferric salts to the VCM. Among these salts is ferric chloride which is an impurity which can victimize an otherwise meticulously operated polymerization process because it produces off-spec poly(vinyl chloride). Another impurity which can have the same deleterious effect is butadiene. In copending U.S. patent application Ser. No. 779,337 filed Sept. 23, 1985, there is disclosed a process for minimizing the formation of ferric chloride. Yet it is ferric chloride, in a critically controlled amount, less than 200 ppm which, in combination with chlorine, is so effective in removing butadiene without the $FeCl_3$ presenting a problem in the subsequent polymerization of the VCM. Yet there is sufficient $FeCl_3$ present to catalyze the chlorination of BD, and the polymerization of BD, without plugging the quench tower.

About a quarter of a century ago, BD was removed by chlorination at a temperature in the range from $-30°$ C. to 20° C. with an excess of chlorine, in the range from 1 to 5 times the stoichiometrically required amount. The stoichiometric amount is two moles of chlorine for each mole of BD, since BD has two double bonds which can be chlorinated. In this temperature range, the process disclosed in U.S. Pat. No. 3,125,607 to Keating et al was based on the discovery that even a large excess of chlorine did not chlorinate the VCl provided it was anhydrous. But the chlorination took too long even when ferric chloride was used to eliminate moisture. When they used a 2:1 mol ratio (stoich) they found it took 200 min to lower the BD conc from 200 ppm to 20 ppm. The problem with using excess chlorine, was that the chlorine not used in chlorination, remained to hamper the subsequent polymerization of the VCM produced. When a small amount of ferric chloride was added to a VCl-BD (200 ppm) mixture they found no apparent effect. So they used $FeCl_3$ to pick up moisture; but the $FeCl_3$ was unavoidably left to contaminate the VCM, it not having been recognized that only a very small amount of left-over $FeCl_3$ could be tolerated.

$FeCl_3$ was later found to polymerize BD in VCl, but the polymerization products were adsorbed in a packed column, and were thus removed (see Japanese patent JP No. 49/33165 [74/33165] Sept. '74). This method of removing the BD was contraindicated if the packed column was to operate as the quench tower of a VCl plant.

More than a decade later U.S. Pat. No. 3,876,714 to Coppens taught a process for the addition of from 0.01 to 5% by wt with respect to EDC which was not converted by the pyrolysis, in such a manner as to obtain a liquid practically free of chloroprene (CP), thus ensuring that all BD and CP were chlorinated.

Soon thereafter, U.S. Pat. No. 3,920,761 to Krome disclosed that the addition of from 0.01 to 1% by weight of chlorine (based on the EDC originally used in the feed to the cracking furnace) by itself, was effective to remove BD as well as half the monovinylacetylene (MVA) and two-thirds the CP, all generated at a cracking severity in the range from 70 to 90%, though the temperature range for chlorination with a superstoichiometric amount of chlorine, may be from $-30°$ to $+150°$ C. But no quench tower was used and the reaction was carried out with no limitation on "hold-up" time, as a receiver was used to store cooled effluent from the cracking furnace. Hold-up time is derived by dividing the average instantaneous liquid volume in the quench tower by the rate of flow of liquid EDC (quench stream).

Nor did they note any stringent requirement for anhydrous conditions, or the use of a salt such as $FeCl_3$ to ensure that such anhydrous conditions be provided. Coppens suggested $FeCl_3$ as a chlorination catalyst but did not suggest how to deal with the polymers of BD which would also be formed. Presumably, Krome recognized the problems associated with using $FeCl_3$ but did not realize that less than 200 ppm $FeCl_3$ would not be injurious to VCM polymerization; nor that it would be an effective catalyst to chlorinate and polymerize BD simultaneously in the operating temperature range of a quench tower.

As is quite evident in either the Coppens or Krome processes, if the cracking severity was 60%, that is, 40% by wt of the EDC was unconverted, then a minimum of 0.4% (4000 ppm) of chlorine would be used. If the BD conc was as high as 200 ppm and it was fully chlorinated, then only 262 ppm chlorine is stoichiometrically required and the remaining excess chlorine must be removed by neutralizing it. This involves the problem of coping with the exces chlorine in the system, not to mention the unnecessary expense.

Moreover, in each of the Coppens and Krome processes, there was no restriction as to hold-up time since a reservoir was used for the chlorination reaction. Further, though Coppens suggested that a chlorination catalyst such as $FeCl_3$ be added to the reservoir, there is no teaching that the EDC/VCl be essentially anhydrous for the $FeCl_3$ to provide its catalytic effect, or that there is a strict limit as to the amount of the $FeCl_3$ which may be carried over into the purified VCM. Particularly noteworthy is the absence of any disclosure as to the polymerization of BD by the $FeCl_3$, known to have an indiscriminate polymerization effect on diene monomers, or, the formation (or lack thereof) of polybutadiene which would have been easily recognized.

SUMMARY OF THE INVENTION

It has been discovered that ferric chloride ($FeCl_3$), a known chlorination and polymerization catalyst for 1,3-butadiene ("BD"), can nevertheless be effectively used in a quench tower, operating under essentially anhydrous conditions, to remove essentially all BD from a crude stream of vinyl chloride (VCl), without plugging the quench tower with polymer, though anhydrous chlorine is used in less than half the stoichiometric amount, in combination with less than 200 ppm $FeCl_3$, provided the amount of BD in the stream is less than 100 ppm, based on the weight of 1,2-dichloroethane (ethylene dichloride or "EDC") in the stream. By "essentially anhydrous" I refer to a moisture concentration in the range from 10 ppm to 50 ppm.

It is therefore a general object of this invention to provide a chlorination process for the removal of BD from a crude VCl stream, using less than half the stoichiometric amount of chlorine than that required to remove all BD, within a maximum 6 min hold-up time in a quench column, so that essentially no free chlorine is left in the VCl, after it is purified in a VCl distillation column; and, simultaneously to polymerize BD not chlorinated without plugging the quench tower, by maintaining a concentration of $FeCl_3$ in the range from 100–200 ppm in the quench tower.

It has also been discovered that purifying VCl to contain no more than 10 ppm BD, within the limitation of a 6 minute hold-up time in a quench column, requires that water be limited to 50 ppm in the effluent from the cracking furnace.

It is also a general object of this invention to provide a process in which the first step is to control the severity of cracking in a cracking (or pyrolysis) furnace for EDC, so that the amount of moisture is less than 50 ppm, and the BD generated is no more than 100 ppm, thus permitting the simultaneous chlorination and polymerization of the BD, substantially without chlorinating the CP, the MVA or the VCl in the effluent, and substantially without plugging the quench tower.

It is a specific object of this invention to inject a sub-stoichiometric ("substoich") amount, less than 100 ppm of anhydrous chlorine, and to maintain from 100–200 ppm of $FeCl_3$ in a quench tower for the effluent of the EDC cracking furnace, so that removal of BD is effected during a maximum 6 min hold-up time in the column, without providing any additional residence time in a storage tank, and before the bottoms from the quench tower is stripped to remove anhydrous hydrochloric acid (HCl).

It is also a specific object of this invention to provide a process for the removal of BD by selective chlorination and polymerization without leaving free chlorine in the VCM (purified VCl), but with no regard to the amount of CP or MVA left therein, since these may be effectively removed by distillation before purification of the VCl.

BRIEF DESCRIPTION OF THE DRAWING

The foregoing and other objects and advantages of my invention will appear more fully from the following description, made in connection with the accompanying drawing of the preferred embodiment of the invention wherein the drawing is a flowsheet of a modified EDC purification section of a VCM plant, in which section a substoich amount of chlorine and sufficient $FeCl_3$ to provide a simultaneous catalytic chlorination and polymerization effect are injected into the quench tower to remove BD without substantially chlorinating other chlorinatable byproducts or VCl.

DETAILED DESCRIPTION OF THE PREFERRED EMBODIMENT

In the preferred embodiment, this invention relates to the vinyl chloride ("VCl") purification portion of a commercial plant. Purification of VCl, to produce product VCM, is a principal step in the operation of a "balanced" VCl process (see *Encyclopedia of Chemical Technology* by Kirk & Othmer, Chap. titled "Vinyl Polymers (Vinyl Chloride)" Vol 23, pg 870, 3d ed. John Wiley & Sons) details of which are well known and incorporated by reference thereto as if fully set forth herein.

Referring to the flowsheet, there is shown a cracking furnace CF in which EDC under a pressure in the range from about 20–25 atm, and a temperature in the range from about 500°–550° C., is cracked as it passes through tubes filled with an inert siliceous packing. The severity of the cracking is controlled so that no more than 100 ppm of BD is present in the effluent, and the concentration of BD in the effluent is continuously measured. This limitation of BD concentration prevails at a severity in the range from about 50–70%, that is, a minor proportion by wt of the effluent, from about 30–50%, is EDC, the remaining being pyrolysis products.

The main pyrolysis products are VCl and HCl which are to be separated. Upon separation in a HCl column 20, the HCl is returned to the oxychlorination section of the balanced EDC plant where it is converted to EDC. In addition to BD, other byproducts produced include MVA and CP, each of which is usually present in an amount greater than the BD. The production of BD is continuously monitored to determine the amount of chlorine which is to be introduced into the quench tower.

The gaseous effluent from the furnace CF flows into the lower portion of quench tower 10 which may have conventional trays, or be packed with Berl saddles or the like. The effluent which consists essentially of from about 20–30% by wt EDC, 35–45% VCM, 35–45% HCl, 100–200 ppm CP, less than 100 ppm MVA, and no more than 100 ppm BD, is flowed countercurrent to a quench stream of liquid EDC at a temperature in the range from about 50°–90° C., introduced through line 11 into the tower, near its top. When the hot gases are quenched, a minor proportion by wt of its components are condensed and leave the quench tower, near its bottom, at a temperature in the range from about 70°–110° C. The major portion is uncondensed effluent which consists essentially of VCl, EDC and HCl vapors and essentially no gaseous chlorine, all of which leave the top of the quench tower through line 14 at a temperature in the range from about 50°–100° C. and are led into an HCl column 20. The quench tower typically operates in the temperature range from about 50°–200° C., though it is preferred to operate it at as low a temperature as is economically feasible.

A scavenger solution of dry liquid chlorine containing anhydrous FeCl$_3$ is introduced into the quench tower 10, near its top, by mixing with a liquid EDC quench stream, introduced through line 11. The stream is sparged over the upper surface of the packing in the quench tower, so that liquid EDC with a predetermined amount of chlorine and FeCl$_3$ in solution, trickles down countercurrent to the flow of the effluent being quenched. The scavenger solution may be introduced at other, or additional locations in the tower, if desired, to ensure that the BD is scavenged within the hold-up time allowed.

It is essential that less chlorine be introduced than one-half the stoichiometric (half-stoich) amount required to chlorinate all the BD, and to avoid substantially chlorinating the CP and the MVA within the window of time defined by the hold-up of liquid containing BD in the quench tower. Deliberately preferentially chlorinating the BD to as great a degree as possible under the conditions of the quench tower is found to be highly practical because both unchlorinated MVA and CP are removable by distillation. As is well known, the danger of chlorinating any VCl under these conditions is essentially reduced to theoretically and practically nearly nothing. With less than a half-stoich amount of chlorine, the effectiveness of chlorination of the BD is maintained without impeding the polymerization of the BD, catalyzed by the FeCl$_3$.

The combination of chlorination and polymerization, each catalyzed to some extent by the very small amount of FeCl$_3$ present, accounts for the high speed of removal of BD monomer. The hold-up time of the liquid (VCl, EDC, contaminants, chlorine and FeCl$_3$) in the quench tower is in the range from 5 to 6 min, which is the critical time within which chlorination and polymerization of the BD must be effected before the liquid bottoms from the quench tower is pumped to the HCl column 20 where HCl is stripped from VCl and EDC. Surprisingly, the chlorinated BD and BD polymers are not deposited on the internals of the quench tower for long enough to form a tower-plugging buildup.

The liquid from the bottom of the quench tower is led through line 12 into the bottom of the HCl column 20; and overhead from the quench tower is led through line 14 into the upper portion of the column 20 to remove HCl. The HCl comes off overhead and is condensed in condenser C20; a portion is refluxed to column 20 and the remainder recycled through line 21 to reactors used in the oxychlorination portion of the VCl plant. The bottoms from HCl column 20 is a VCl rich stream, and essentially free of BD, provided the moisture in the quench tower is critically limited to 50 ppm. By "essentially free of BD" I refer to the stream containing so low a concentration of BD that when all the BD is taken overhead in a VCl column 30, the concentration of BD is less than 10 ppm which is not deleterious to the subsequent polymerization of finished VCM product.

The upper limit of concentration of moisture in the quench tower is critical, because at higher than 50 ppm moisture, the polymerization effect of the FeCl$_3$ is effectively nullified, as is its catalytic effect on the chlorination of BD. The bottoms stream from the HCl column, referred to as an "anhydrous VCl/EDC stream", contains all the FeCl$_3$ introduced into the system, and also the chlorinated BD and BD polymers. This stream is flowed through line 22 to a VCl column 30.

Though the overhead from the VCl column 30 contains all the unchlorinated and unpolymerized BD left in stream 22, the overhead is essentially BD-free (less than 10 ppm). The overhead stream is condensed in condenser C30 and a portion refluxed to column 30, the remaining portion being flowed through line 31 to VCM storage. Since the BD conc in the overhead is so low that it is "within spec" for product VCM, the VCl column 30 may be operated at a very low reflux ratio, thus saving energy and improving the economics of the process. However, the overhead may still contain about 10 ppm water and some HCl which is generated by decomposition of some of the chlorinated compounds in the reboiler (not shown) of the column 30. It is therefore flowed through line 31 to a VCl stripper 40, and thence to conventional caustic beds, or, a cold caustic wash system indicated generally by reference numeral 50, for removing any traces of water (less than 50 ppm), and HCl, and possibly a trace of chlorine, to produce finished VCM. This system is described in the aforesaid '337 patent application, details of which are incorporated by reference thereto as if fully set forth herein.

All liquid lines are under pressure since the boiling point of VCl under atmospheric presure is 8° F. A line 32 carries the bottoms from the column 30 to a EDC recovery section where unconverted EDC is recovered for recycle to the cracking furnace. A portion of this bottoms stream may be recycled to the quench tower as liquid EDC quench, through line 33, preferably after it is cooled in heat exchanger HE to a temperature in the range from about 30°–50° C., the cooler the better to quench the hot gaseous effluent from the cracking furnace CF and keep any unreacted BD in the bottoms from the quench tower.

On occasion, due to heat exchange limitations, it is desirable to operate the quench tower at higher temperatures than 110° C., up to about 200° C. In this upper portion of the tower's operating range, there will be a higher proportion of CP and MVA chlorinated by the chlorine introduced. Therefore, greater than a half-stoichiometric amount of chlorine is desirably added, but the amount is still always less than stoichiometric, that is, sub-stoich. It will also be found that, in the upper operating range, polymerization of BD and other monomers polymerizable with FeCl$_3$, will also be accelerated.

Typically, EDC is recovered for recycling to the process by conventional distillation; the result is the separation of essentially pure EDC in the overhead, and heavy ends in the bottoms which are incinerated or otherwise disposed of. The liquid EDC recycle for the quench tower may be taken from the overhead of the EDC recovery column (not shown), if desired.

The invention is illustrated by the following example in which all parts refer to parts by weight, as do references to percentages.

EXAMPLE

In a VCl plant capable of producing 3 million lb/day of VCl, 330,500 lb/hr of EDC are fed to a cracking furnace at a temperature of 525° C. and a pressure of 22 atm., and the severity of cracking is maintained at about 60% so that 40% of the EDC is not cracked. The effluent from the furnace is led into plural quench towers in which the combined instantaneous average volume of liquid is 395 ft$^3$. The combined flow of the liquid EDC quench streams to the quench towers is 67 ft$^3$/min., so that the hold-up is 5.9 min. The mean operating temperature of the quench tower is 80° C. The BD content of the effluent is 100 ppm, which determines the amount of chlorine to be added, and the CP and MVA concentrations are higher. Small concentrations of lower alkyl chlorides, 1,1-dichloroethane, and other chlorinated hydrocarbons such as 1,2,4-trichlorobutane, 1,2-dichlorobutane, 1,1,2-trichloroethane, trichloroethylene and the like are not monitored as they do not affect the amount of chlorine to be added.

The liquid EDC quench streams contain a total of 100 ppm dry chlorine, and 110 ppm anhydrous FeCl$_3$ in solution.

Bottoms from the quench tower and HCl recycle from the overhead of the VCl stripper 40 are together about 258,000 lb/hr through line 12, and the overhead 14 from the quench tower is about 92,500 lb/hr. Overhead from the HCl column 20 is about 72,600 lb/hr recycled to the oxychlorination reactors, and the bottoms flow in line 22 is 277,900 lb/hr, the BD content of which is 10 ppm. This bottoms 22 is flowed into the bottom of the VCl column 30. The draw-off 31 from the overhead of the VCl column, to the VCl stripper 40 is 145,000 lb/hr, about 20,000 lb/hr of which is predominantly HCl recycled to the HCl column 20. The balance of 125,000 lb/hr of stripped VCl is sent through line 42 to the cold caustic wash system 50.

I claim:

1. A process for purifying vinyl chloride generated in a dichlorothane cracking furnace's effluent containing contaminant amounts of butadiene, chloroprene and monovinylacetylene, said process comprising,
   (i) operating the cracking furnace at a temperature in the range from about 500°–550° C., at a pressure in the range from about 20–30 atm, and at a cracking severity in the range from about 50–70% so as to maintain a concentration of butadiene no more than 100 ppm, and of water no more than 50 ppm in the furnace's effluent;
   (ii) continuously measuring the concentration of butadiene in said effluent;
   (iii) quenching said effluent in a quench tower operating in the range from about 50°–200° C. by flowing 1,2-dichloroethane downwards through said tower countercurrent to said effluent;
   (iv) introducing less than the stoichiometric amount of liquid chlorine, based on the measured amount of butadiene in the effluent, in combination with from 100–200 ppm ferric chloride based on the dichloroethane quench stream near the top of the quench tower;
   (v) polymerizing a portion of the butadiene and simultaneously chlorinating the remaining portion preferentially relative to the chloroprene and the monovinylacetylene, so that essentially all butadiene is removed during a hold-up time of no more than 6 minutes in the quench tower, without polymer buildup interfering with the continuous operation of the quench tower under essentially anhydrous conditions; and,
   (vi) in a vinyl chloride column, distilling vinyl chloride containing less than 10 ppm butadiene as the overhead and returning a portion of essentially butadiene-free bottoms from said vinyl chloride column to the quench tower.

2. The process of claim 1 wherein said hold-up time is in the range from about 5 but less than 6 min.

3. The process of claim 2 wherein said operating temperature of the quench tower is in the range from about 70° to about 110° C. and said amount of liquid chlorine introduced is less than one-half the stoichiometric amount.

* * * * *